(12) United States Patent
Lee et al.

(10) Patent No.: US 9,155,702 B2
(45) Date of Patent: Oct. 13, 2015

(54) COMPOSITION AND MICROSPHERE FOR CONTROLLED-RELEASE OF EXENDIN, AND METHOD PREPARING THE SAME

(75) Inventors: Hee-Yong Lee, Daejeon (KR); Eun-Young Seol, Daejeon (KR); Joon-Sik Kim, Daejeon (KR); Mi-Jin Baek, Daejeon (KR); Jung-Soo Kim, Daejeon (KR); Ju-Han Lee, Daejeon (KR); Yeon-Jin Chae, Daejeon (KR); Chae-Jin Lim, Daejeon (KR); Mi-Young Baek, Daejeon (KR); Ho-Il Choi, Daejeon (KR)

(73) Assignee: PEPTRON CO., LTD, Daejeon (KR)

( * ) Notice: Subject to any disclaimer, the term of this patent is extended or adjusted under 35 U.S.C. 154(b) by 281 days.

(21) Appl. No.: 12/532,311

(22) PCT Filed: Jan. 22, 2008

(86) PCT No.: PCT/KR2008/000397
§ 371 (c)(1),
(2), (4) Date: Sep. 21, 2009

(87) PCT Pub. No.: WO2008/117927
PCT Pub. Date: Oct. 2, 2008

(65) Prior Publication Data
US 2010/0136126 A1  Jun. 3, 2010

(30) Foreign Application Priority Data
Mar. 27, 2007 (KR) .................. 10-2007-0029586

(51) Int. Cl.
*A61K 9/16* (2006.01)
*A61K 9/00* (2006.01)
*A61K 9/19* (2006.01)
*A61K 38/22* (2006.01)
*A61K 9/50* (2006.01)
*A61K 47/26* (2006.01)
*A61K 47/38* (2006.01)

(52) U.S. Cl.
CPC ............. *A61K 9/1647* (2013.01); *A61K 9/0024* (2013.01); *A61K 9/19* (2013.01); *A61K 9/5015* (2013.01); *A61K 9/5026* (2013.01); *A61K 38/2278* (2013.01); *A61K 47/26* (2013.01); *A61K 47/38* (2013.01)

(58) Field of Classification Search
CPC ..... A61K 9/0024; A61K 9/1647; A61K 9/19; A61K 9/5026; A61K 47/26; A61K 47/38; A61K 9/5015; A61K 38/2278
See application file for complete search history.

(56) References Cited

U.S. PATENT DOCUMENTS

| 4,389,330 | A | 6/1983 | Tice et al. |
| 5,271,961 | A * | 12/1993 | Mathiowitz et al. ...... 427/213.31 |
| 7,164,005 | B2 | 1/2007 | Costantino |
| 2006/0034923 | A1 | 2/2006 | Li |
| 2006/0093680 | A1 * | 5/2006 | Humar et al. .................. 424/490 |
| 2008/0299168 | A1 * | 12/2008 | Dadey et al. .................. 424/423 |

FOREIGN PATENT DOCUMENTS

| CN | 1347327 | 5/2002 | |
| JP | 09-315975 | 12/1997 | |
| JP | 11-79976 | 3/1999 | |
| JP | 2002-255857 | 9/2002 | |
| KR | 10-2003-0081179 | 10/2003 | |
| RU | 2104039 | 2/1998 | |
| WO | 00/41546 | 7/2000 | |
| WO | 01/51078 | 7/2001 | |
| WO | 2005/102293 | * 11/2005 | ............... A61K 9/50 |
| WO | 2005/110425 | 11/2005 | |

OTHER PUBLICATIONS

Yeo et al, "Control of Encapsulation Efficiency and Initial Burst in Polymeric Microparticle Systems," Arch Pharm Res vol. 27, No. 1, 1-12, 2004.*
Geraghty et al, "The primary structure of a plant storage protein: zein," Nucleic Acids Research 9(19): 5163-5174 (1981).*
Huang YY, Chung TW, Tzeng TW, "A method using biodegradable polylactides/polyethylene glycol for drug release with reduced initial burst," International Journal of Pharmaceutics, vol. 182, p. 93-100 (May 1999).
Xiao Huang, Christopher S. Brazel "On the importance and mechanisms of burst release in matrix-controlled drug delivery systems" Journal of Controlled Release, vol. 73, p. 121-136 ( Jun. 2001).
European Patent Office, the extended search report of the corresponding application, European Patent Application No. 08712168.7 (Jun. 13, 2013).

* cited by examiner

*Primary Examiner* — Suzanne Ziska
(74) *Attorney, Agent, or Firm* — Lex IP Meister, PLLC

(57) ABSTRACT

A controlled-release composition and controlled-release microspheres containing an exendin as an active ingredient, and a method of preparing the same are provided. More specifically, a controlled-release composition containing an exendin as an active ingredient, a biodegradable polymer with a specific viscosity, and coating materials, having high bioavailability and showing sustained release of the active ingredient in an effective concentration for a certain period without an excessive initial burst of the active ingredient; controlled-release microspheres containing a core including an exendin as an active ingredient and a biodegradable polymer, and a coating layer coating the core; and a method of preparing controlled-release microspheres including the steps of mixing an exendin, a biodegradable polymer, and a solvent, removing the solvent from the mixture to prepare hardened microspheres, and coating the hardened microspheres to form a coating layer on the surface of each microsphere, are provided.

11 Claims, 7 Drawing Sheets

SEQUENCE LISTING

```
<160> NUMBER OF SEQ ID NOS: 6

<210> SEQ ID NO 1
<211> LENGTH: 39
<212> TYPE: PRT
<213> ORGANISM: Artificial Sequence
<220> FEATURE:
<223> OTHER INFORMATION: amino acid sequence of Exendin-3

<400> SEQUENCE: 1

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: amino acid sequence of Exendin-4

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
    35
```

```
<210> SEQ ID NO 3
<211> LENGTH: 28
<212> TYPE: PRT
<213> ORGANISM: Artificial Sequence
<220> FEATURE:
<223> OTHER INFORMATION: amino acid sequence of Exendin-4 variant (1-28)

<400> SEQUENCE: 3

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 4
<211> LENGTH: 30
<212> TYPE: PRT
<213> ORGANISM: Artificial Sequence
<220> FEATURE:
<223> OTHER INFORMATION: amino acid sequence of Exendin-4 variant (1-30)

<400> SEQUENCE: 4

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: amino acid sequence of Exendin-4 variant

<400> SEQUENCE: 5

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro
            20                  25                  30

<210> SEQ ID NO 6
<211> LENGTH: 39
<212> TYPE: PRT
<213> ORGANISM: Artificial Sequence
<220> FEATURE:
<223> OTHER INFORMATION: amino acid sequence of 14Leu25Phe Exendin-4
      variant

<400> SEQUENCE: 6

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
            35
```

COMPOSITION AND MICROSPHERE FOR CONTROLLED-RELEASE OF EXENDIN, AND METHOD PREPARING THE SAME

CROSS REFERENCE TO RELATED APPLICATION

This application claims priority to and the benefit of Korean Patent Application No. 10-2007-0029586 filed on Mar. 27, 2007, which is hereby incorporated by reference for all purposes as if fully set forth herein.

BACKGROUND OF THE INVENTION (a) Field of the Invention

The present invention relates to a controlled-release composition and a controlled-release microsphere containing an exendin as an active ingredient, and a method of preparing the same.

(b) Description of the Related Art

Exendins are glucagon-like peptide 1 (GLP-1) agonists acting as a GLP-1 hormone in the body, and exendin-4 has 53% sequence homology with the amino acid sequence of GLP-1(7-36)NH$_2$ (Goke, et al., J. Biol. Chem., 268: 19650-19655, 1993).

GLP-1, a representative incretin hormone, is a peptide secreted from L cells in the intestine, is secreted when food inflow into the digestive track occurs, and lowers the blood-sugar level by stimulating insulin secretion from pancreatic beta-cells (Orskov, et al., Diabetes, 42:658-661, 1993). Further, GLP-1 inhibits glucagon release from pancreatic alpha-cells (D'Alessio, et al., J. Clin. Invest., 97:133-138, 1996), and increases gastric-intestinal emptying time resulting in inhibition of food intake (Schira, et al., J. Clin. Invest., 97:92-103, 1996). GLP-1 has functions not only to stimulate insulin secretion from pancreatic beta-cells, but also to increase proliferation rate and survival rate of beta cells (Buteau, et al., Diabetologia, 42:856-864, 1999). However, GLP-1 loses its function by cleavage of its N-terminal region by dipeptidyl peptidase-4 (DPP-4), and has a very short half-life of about 2 minutes (Pridal, et al., Eur. J. Drug. Metab. Pharmacokinet., 21:51-59, 1996; Deacon, et al., Diabetes, 47:764-769, 1998).

Exendins have been known to increase insulin secretion depending on the blood-sugar level in the body, to inhibit postprandial glucagon release, and to lower gastric-intestinal emptying rate resulting in inhibition of food intake. In addition, exendins have an advantage of having a longer half-time than GLP-1, since exendin, unlike GLP-1, is not cleaved at the N-terminal region by DPP-4, and thus exendins can exhibit its function in the body for a longer time than GLP-1 (Thum, et al., Exp. Clin. Endocrinol. Diabetes., 110:113-118, 2002). Exendins are found in salivary secretions of the Gila monster and the Mexican Beaded Lizard, wherein exendin-3 is found in a Mexican Beaded Lizard, *Heloderma horridum*, and exendin-4 is found in a Gila monster, *Heloderma suspectum* (Eng, J., et al., J. Biol. Chem., 265:20259-62, 1990; Eng., J., et al., J. Biol. Chem., 267:7402-05, 1992).

It has been confirmed by intraperitoneal injections of exendin-4 into diabetic ob/ob mice once per a day that exendin-4 has a prolonged effect of lowering the blood-sugar level (Greig et al., Diabetologia 42:45-50, 1999). Recently, exendin-4 has been formulated as an injection agent that is subcutaneously injected twice daily at a dose of 5 μg or 10 μg. Although exendin is stable against the DPP-4 enzyme, it has been known to cause side effects such as vomiting, nausea, headaches, and the like, when it is subcutaneously injected to a human at a dose of 0.2 μg/kg or more (Drug Development Research, 53:260-267, 2001). For administration of exendins, the dose limit due to the side effects by initial burst and initial high blood concentration is the biggest obstacle to development of a controlled-release agent of exendin.

Generally, a controlled-release agent of an aqueous drug exhibits a very high release at the initial stage after administration, and there have been various studies to decrease the excessive initial burst. In particular, in developing a controlled-release agent of exendins, decreasing the initial burst is indispensable for preventing side effects such as vomiting, nausea, headaches, and the like caused by the excessive initial burst.

In order to decrease the initial burst of controlled-release microspheres containing octreotide having a therapeutic effect on acromegaly and the like, there has been a study to prepare microspheres by preparing a primary emulsion of the drug together with glucose, and then performing a double emulsion method. In this study, it has been revealed that the initial burst can be decreased by loading the drug together with glucose. However, under a preparation condition in which the initial burst from microspheres is about 5%, the addition of glucose cannot lead to an increase in loading amount, and rather increases the initial burst (J. Wang et al., Biomaterials, 25:1919-1927, 2004).

Therefore, the technique disclosed in the above document is difficult to apply to preparation of a controlled-release formulation of an exendin wherein the initial burst should be 5% or below to decrease side effects caused by the initial burst.

U.S. Pat. No. 7,164,005 and US2005/0271702 disclose a method of preparing exendin-containing microspheres by a phase-separation method using a poly(lactide-co-glycolide) (PLGA) polymer where the ratio of lactide:glycolide is 50:50. In the above documents, polymer 3A (IV=0.38 dL/g), polymer 4A (IV=0.42 dL/g), and the like, particularly polymer 4A, provided by Alkermes Inc., are used as the polymer. In the above documents, the microspheres are prepared by mixing a peptide drug with salting-out components such as ammonium sulfate and sugars such as sucrose and mannitol to prepare a primary emulsion, in order to improve the bioavailability of the microspheres consisting of an exendin and polymer 3A, or 4A, and the stability of the peptide drug. That is, the documents intend to improve the bioavailability by adding additives such as sugars, ammonium sulfate, and the like, thereby allowing sufficient release of an exendin from the polymer matrix. As a result, the bioavailability can be improved to some degree, but the Cmax value is also high, thereby generating the problem of side effects caused by a high initial burst. That is, when the bioavailability becomes high, the initial burst becomes excessive, while when the initial burst becomes low, the bioavailability becomes low.

As described above, the existing techniques of preparing a controlled release microsphere have limitations in that the prepared microsphere has an excessively high initial burst and insufficient bioavailability to be applied to preparation of exendin-containing controlled-release microspheres that require minimization of side effects caused by high initial burst together with improved bioavailability.

Therefore, to solve the above problems, it is necessary to develop a biodegradable exendin-containing formulation exhibiting a low initial burst and improved bioavailability.

SUMMARY OF THE INVENTION

In order to meet the above needs, it is an object of the present invention to provide a controlled-release agent with high bioavailability containing an exendin as an active ingre-

DETAILED DESCRIPTION OF THE PREFERRED EMBODIMENTS

Figure 1:
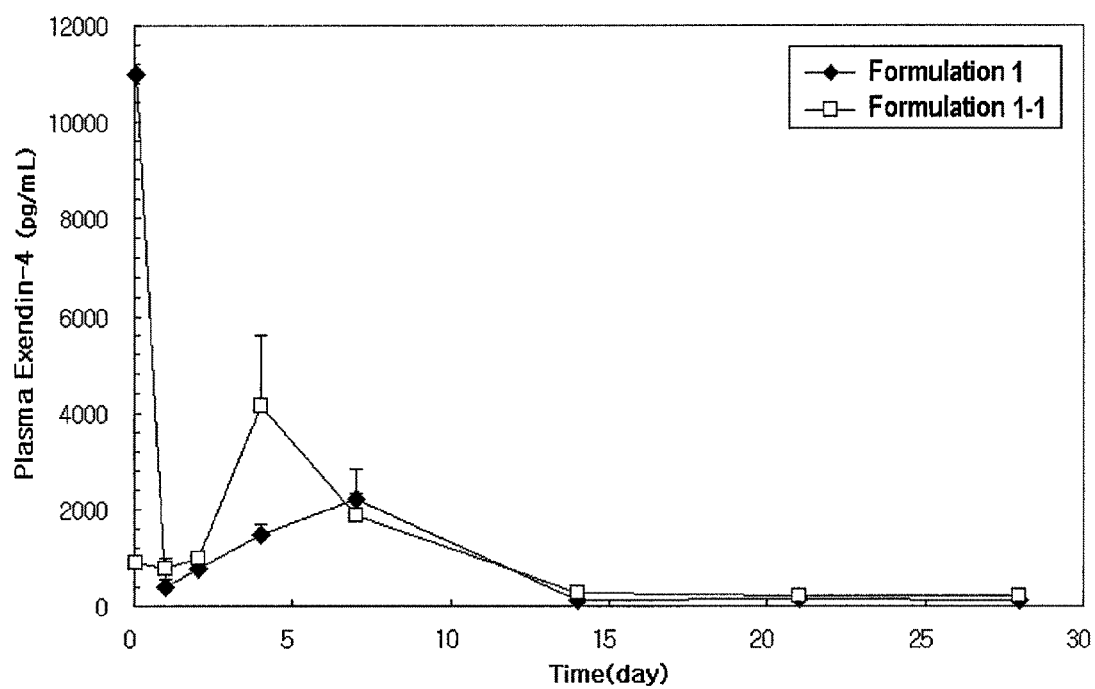
FIG. 1 is a graph showing a change in blood drug concentration in rats depending on the presence of a coating layer in an exendin-containing formulation of RG502H.

A more complete appreciation of the invention, and many of the attendant advantages thereof, will be readily apparent as the same becomes better understood by reference to the following detailed description.

The present invention relates to an exendin-containing controlled-release microsphere composition with high bioavailability and a minimized drug initial burst when administered to the body.

Korean Patent No. 140209 discloses a method of preparing a microsphere by dissolving an aqueous drug with specific basic organic materials to prepare a primary emulsion, and then performing a double emulsion method, in order to inhibit initial burst of the aqueous drug. The above document discloses increasing the drug loading efficiency and inhibiting an unnecessary high initial burst by forming a strong layer by interaction between acidic residues of biodegradable polymers and basic residues of drug. As disclosed in the above document, the above method may be useful in preparing a controlled-release composition containing a basic or neutral polypeptide, such as LHRH, TRH, and derivatives thereof. However, the method may not be useful depending on the characteristics of drugs to be loaded, in particular, in preparing a controlled-release composition containing an acidic drug with relatively larger molecular weight compared with LHRH and TRH, such as an exendin and the like. Further, in the above method, the addition of basic materials causes increased porosity of the prepared microsphere surface, and thus the method is not suitable for preparing a controlled-release formulation containing an exendin that exhibits various side effects caused by the initial burst.

The present inventors confirmed that microspheres having high bioavailability and no side effects from an excessive initial burst can be formed by coating them with specific coating materials during or after preparing exendin-containing microspheres using biodegradable polymers as carriers, to complete the present invention.

First, the present invention provides a controlled-release composition containing an exendin as an active ingredient, a biodegradable polymer with a specific viscosity, and coating materials, having high bioavailability and showing sustained release of the active ingredient in an effective concentration for a certain period without an excessive initial burst of the active ingredient.

In another aspect, the present invention provides a controlled-release microsphere containing a core including exendin as an active ingredient and a biodegradable polymer; and coating layer coating the core.

Hereinafter, the present invention is more concretely described.

In the present invention, the exendin may be one or more selected from the group consisting of exendin-3 (SEQ ID NO: 1), exendin-4 (SEQ ID NO: 2), and fragments, derivatives, and pharmaceutically acceptable salts thereof.

The exendin derivatives may be a compound represented by following Chemical Formula I, or its pharmaceutically acceptable salt.

(Chemical Formula I)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28 -Z1, wherein:
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala, or Arg;
Xaa21 is Ala, Leu, or Lys-NHc-R (wherein R is Lys, Arg, or a C1-C10 straight chain or branched alkanoyl);
Xaa22 is Ala, Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
Xaa27 is Ala or Lys;
Xaa28 is Ala or Asn; and
Z1 is —OH,
—NH2,
Gly-Z2,
Gly Gly-Z2,
Gly Gly Xaa31-Z2, Gly Gly Xaa31 Ser-Z2,
Gly Gly Xaa31 Ser Ser-Z2,
Gly Gly Xaa31 Ser Ser Gly-Z2,
Gly Gly Xaa31 Ser Ser Gly Ala-Z2,
Gly Gly Xaa31 Ser Ser Gly Ala Xaa36-Z2,
Gly Gly Xaa31 Ser Ser Gly Ala Xaa36 Xaa37-Z2,
Gly Gly Xaa31 Ser Ser Gly Ala Xaa36 Xaa37 Xaa38-Z2, or
Gly Gly Xaa31 Ser Ser Gly Ala Xaa36 Xaa37 Xaa38 Xaa39-Z2, (wherein Xaa31, Xaa36, Xaa37, and Xaa38 are independently Pro, homoproline, 3Hyp, 4Hyp, thioproline, N-alkylglycine, N-alkylpentylglycine, or N-alkylalanine, Xaa39 is Ser, or Tyr, and more preferably Ser, and Z2 is —OH, or —NH$_2$), provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala, and when Xaa1 is His, Arg, or Tyr, at least one of Xaa3, Xaa4, and Xaa9 is Ala.

Preferred N-alkyl groups for N-alkylglycine, N-alkylpentylglycine, and N-alkylalanine may include lower alkyl groups preferably of 1 to about 6 carbon atoms, more preferably of 1 to 4 carbon atoms. The compound represented by Chemical Formula I may include compounds identified in Examples 1 to 89 (Compounds I to 89, respectively), and the corresponding compounds identified in Examples 104 and 105 in PCT application Serial No. PCT/US98/24273 filed on Nov. 13, 1998, entitled "Novel Exendin Agonist Compounds", which is hereby incorporated by reference.

Preferred exendin derivatives of Chemical Formula I may include those wherein Xaa1 is His, Ala, Norval, or 4-imidazopropionyl, more preferably, Xaa1 is His, Ala, or 4-imidazopropionyl, and even more preferable, Xaa1 is His or 4-imidazopropionyl.

Preferred exendin derivatives of Chemical formula I may be those wherein Xaa2 is Gly.

Preferred exendin derivatives of Chemical Formula I may be those wherein Xaa3 is Ala.

Preferred exendin derivatives of Chemical Formula I may be those wherein Xaa4 is Ala.

Preferred exendin derivatives of Chemical Formula I may be those wherein Xaa9 is Ala.

Preferred exendin derivatives of Chemical Formula I may be those wherein Xaa14 is Leu, pentylglycine, or Met.

Preferred exendin derivatives of Chemical Formula I may be those wherein Xaa21 is Lys-NHϵ-R (wherein R is Lys, Arg, or C1-C10 straight chain or branched alkanoyl).

Preferred exendin derivatives of Chemical Formula I may be those wherein Xaa25 is Trp or Phe.

Preferred exendin derivatives of Chemical Formula I may be those wherein Xaa6 is Ala, Phe, or naphthylalanine, Xaa22 is Phe or naphthylalanine, and Xaa23 is Ile or Val. Further, preferred exendin derivatives of Chemical Formula I may be those wherein Xaa31, Xaa36, Xaa37, and Xaa38 are independently selected from the group consisting of Pro, homoproline, thioproline, and N-alkylalanine, and more preferably Z1 is —NH2 and Z2 is —NH2.

In another aspect, preferred exendin derivatives of Chemical Formula I may be those wherein Xaa1 is Ala, His, or Tyr, and more preferably Ala or His; Xaa2 is Ala or Gly; Xaa6 is Phe or naphthylalanine; Xaa14 is Ala, Leu, pentylglycine, or Met; Xaa22 is Phe or naphthylalanine; Xaa23 is Ile or Val; Xaa31, Xaa36, Xaa37, and Xaa38 are independently selected from the group consisting of Pro, homoproline, thioproline, and N-alkylalanine, and Xaa39 is Ser or Tyr, and more preferably Ser; and preferably Z1 is —NH2.

According to an especially preferred aspect, especially preferred exendin derivatives of Chemical Formula I may be those wherein Xaa1 is His or Ala; Xaa2 is Gly or Ala; Xaa3 is Ala, Asp, or Glu; Xaa4 is Ala or Gly; Xaa5 is Ala or Thr; Xaa6 is Phe or naphthylalanine; Xaa7 is Thr or Ser; Xaa8 is Ala, Ser, or Thr; Xaa9 is Ala, Asp, or Glu; Xaa10 is Ala, Leu, or pentylglycine; Xaa11 is Ala or Ser; Xaa12 is Ala or Lys; Xaa13 is Ala or Gln; Xaa14 is Ala, Leu, Met, or pentylglycine; Xaa15 is Ala or Glu; Xaa16 is Ala or Glu; Xaa17 is Ala or Glu; Xaa19 is Ala or Val; Xaa20 is Ala or Arg; Xaa21 is Ala or Leu; Xaa22 is Phe or naphthylalanine; Xaa23 is Ile, Val, or tert-butylglycine; Xaa24 is Ala, Glu, or Asp; Xaa25 is Ala, Trp, or Phe; Xaa26 is Ala or Leu; Xaa27 is Ala or Lys; Xaa28 is Ala or Asn; Z1 is —OH, —NH2, Gly-Z2, Gly Gly-Z2, Gly Gly Xaa31-Z2, Gly Gly Xaa31 Ser-Z2, Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2; Xaa31, Xaa36, Xaa37, and Xaa38 are independently Pro, homoproline, thioproline, or N-methylalanine; Xaa39 is Ser or Tyr, and more preferably Ser; and Z2 is —OH or —NH2, provided that no more than three of Xaa3, Xaa5, Xaa6, Xaa8, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala, and when Xaa1 is His, Arg, or Tyr, at least one of Xaa3, Xaa4, and Xaa9 may be Ala.

Especially preferred compounds of Chemical Formula I may include those having the amino acid sequences of SEQ ID Nos: 5 to 93 set forth in PCT application Serial No. PCT/US98/25728, or those set forth in U.S. Provisional Application 60/066,029, which are hereby incorporated by reference.

According to an especially preferred aspect, provided are compounds where Xaa14 is Leu, Ile, Val, or pentylglycine, and more preferably Leu or pentylglycine; and Xaa25 is Ala, Phe, Tyr, or naphthylalanine, and more preferably Phe or naphthylalanine. These compounds will be less susceptible to oxidative degradation, both in vitro and in vivo, as well as during synthesis of the compound.

In another aspect, the exendin derivatives may also include the compounds represented by Chemical Formula II or their pharmaceutically acceptable salts.

(Chemical Formula II)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

X1-Z1, wherein
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;

Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHϵ-R (wherein, R is Lys, Arg, C1-C10 straight chain or branched alkanoyl, or cycloalleylalkanoyl);
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
X1 is Lys Asn, Asn Lys, Lys-NHϵ-R Asn, Asn Lys-NHϵ-R, Lys-NHϵ-R Ala, Ala Lys-NHϵ-R (wherein R is Lys, Arg, a C1-C10 straight chain or branched alkanoyl, or cycloalkylalkanoyl);
Z1 is —OH,
—NH2,
Gly-Z2,
Gly Gly-Z2,
Gly Gly Xaa31-Z2,
Gly Gly Xaa31 Ser-Z2,
Gly Gly Xaa31 Ser Ser-Z2,
Gly Gly Xaa31 Ser Ser Gly-Z2,
Gly Gly Xaa31 Ser Ser Gly Ala-Z2,
Gly Gly Xaa31 Ser Ser Gly Ala Xaa36-Z2,
Gly Gly Xaa31 Ser Ser Gly Ala Xaa36 Xaa37-Z2,
Gly Gly Xaa31 Ser Ser Gly Ala Xaa36 Xaa37 Xaa38-Z2, or
Gly Gly Xaa31 Ser Ser Gly Ala Xaa36 Xaa37 Xaa38 Xaa39-Z2,
(wherein Xaa31, Xaa36, Xaa37, and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr, and Z2 is —OH or —NH$_2$),
provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala, and when Xaa1 is His, Arg, Tyr, or 4-imidazopropionyl, at least one of Xaa3, Xaa4, and Xaa9 is Ala.

Preferred exendin derivatives of Chemical Formula II may include those wherein Xaa1 is His, Ala, Norval, or 4-imidazopropionyl, preferably His, 4-imidazopropionyl, or Ala, and more preferably His, or 4-imidazopropionyl.

Preferred exendin derivatives of Chemical Formula II may be those wherein Xaa2 is Gly.

Preferred exendin derivatives of Chemical Formula II may be those wherein Xaa4 is Ala.

Preferred exendin derivatives of Chemical Formula II may be those wherein Xaa9 is Ala.

Preferred exendin derivatives of Chemical Formula II may be those wherein Xaa14 is Leu, pentylglycine, or Met.

Preferred exendin derivatives of Chemical Formula II may be those wherein Xaa25 is Trp or Phe.

Preferred exendin derivatives of Chemical Formula II may be those wherein Xaa6 is Ala, Phe, or naphthylalanine, Xaa22 is Phe or naphthylalanine, and Xaa23 is Ile or Val.

Preferred exendin derivatives of Chemical Formula II may be those wherein Z1 is —NH2.

Preferred exendin derivatives of Chemical Formula II may be those wherein Xaa31, Xaa36, Xaa37, and Xaa38 are independently selected from the group consisting of Pro, homoproline, thioproline, and N-alkylalanine.

Preferred exendin derivatives of Chemical Formula II may be those wherein Xaa39 is Ser or Tyr, and preferably Ser.

Preferred exendin derivatives of Chemical Formula II may be those wherein Z2 is —NH2.

Preferred exendin derivatives of Chemical Formula II may be those wherein Z1 is —NH2.

Preferred exendin derivatives of Chemical Formula II may be those wherein Xaa21 is Lys-NHϵ-R (wherein, R is Lys, Arg, or C1-C10 straight chain or branched alkanoyl).

Preferred exendin derivatives of Chemical Formula II may be those wherein X1 is Lys Asn, Lys-NHϵ-R Asn, or Lys-NHϵ-R Ala (wherein R is Lys, Arg, or a C1-C10 straight chain or branched alkanoyl).

Preferred exendin derivatives of Chemical Formula II may include compounds having the amino acid sequences identified as SEQ ID Nos: 95-110 set forth in WO99/025728. The exendin derivatives of Chemical Formula II may include compounds having the amino acid sequences identified as SEQ ID Nos: 5-93, as described in PCT application PCT/US98/24210, filed Nov. 13, 1998, entitled "Novel Exendin Agonist Compounds". In another aspect, the exendin derivatives of Chemical Formula II may include compounds having the amino acid sequences identified as SEQ ID Nos: 37-40 set forth in WO99/007404. The above documents are hereby incorporated by reference.

The abbreviations used in Chemical Formula I and II stand for the following.
"ACN" and "CH$_3$CN" refer to acetonitrile.
"Boc", "tBoc", and "Tboc" refer to t-butoxy carbonyl.
"DCC" refers to N,N'-dicyclohexylcarbodiimide.
"Fmoc" refers to fluorenylmethoxycarbonyl.
"HBTU" refers to 2-(1H-benzotriazol-1-yl)-1,1,3,3,-tetramethyluronium hexafluorophosphate.
"HOBt" refers to 1-hydroxybenzotriazole monohydrate.
"homoP" and "hPro" refer to homoproline.
"MeAla" and "Nme" refer to N-methylalanine.
"naph" refers to naphthylalanine.
"pG" and "pGly" refer to pentylglycine.
"tBuG" refers to tertiary-butylglycine.
"ThioP" and "tPro" refer to thioproline.
"3Hyp" refers to 3-hydroxyproline.
"4Hyp" refers to 4-hydroxyproline.
"NAG" refers to N-alkylglycine.
"NAPG" refers to N-alkylpentylglycine.
"Norval" refers to norvaline.

In a preferable embodiment, the exendin fragments or derivatives may have a C-terminus substituted or non-substituted with an amide group, and may be selected from the group consisting of exendin-4(1-28) (SEQ ID NO: 3), exendin-4(1-28) amide, exendin-4(1-30) (SEQ ID NO: 4), exendin-4(1-30) amide, exendin-4(1-31) (SEQ ID NO: 5), exendin-4(1-31) amide, $^{14}$Leu$^{25}$Phe exendin-4(SEQ ID NO: 6), $^{14}$Leu$^{25}$Phe exendin-4 amide, and their pharmaceutically acceptable salts.

According to the preferable embodiment, the controlled-release composition or microspheres may contain exendin as an active ingredient in the amount of 0.1 to 10 parts by weight, and more preferably at 0.8 to 6 parts by weight, based on 100 parts by weight of the composition or microsphere containing exendin, biodegradable polymers, and coating materials. When the amount of exendin contained in the composition or microspheres according to the present invention is lower than the above range, the efficient effect of exendin cannot be obtained, and when the amount of exendin is higher than the above range, the initial burst of exendin is increased, thereby causing side effects due to an excessive initial burst, and thus it is preferable that the amount of exendin is within the above range.

The biodegradable polymer refers to all polymers that do not harm human beings, because when it is administered into the body, it can be slowly degraded and excreted. The biodegradable polymer may include one or more selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate, and copolymers of one or more polymers and polyethylenglycol (PEG), wherein the one or more polymers may be in the form of a copolymer or a simple mixture.

For example, the biodegradable polymer may be one or more selected from the group consisting of poly(lactide-co-glycolide)s (PLGA) consisting of RG502H (IV=0.16 to 0.24 dL/g), RG503H (IV=0.32 to 0.44 dL/g), and RG504H (IV=0.45 to 0.60 dL/g), having the lactide:glycolide ratio of 1:1, and RG752H (IV=0.14 to 0.22 dL/g) having the lactide:glycolide ratio of 75:25, polylactides (PLA), R202H (IV=0.16 to 0.24 dL/g) and R203H (IV=0.25 to 0.35 dL/g), which are provided by Boehringer-Ingelheim company, Germany; poly(lactide-co-glycolide)s, 5050DL 2A (IV=0.15 to 0.25 dL/g), 5050DL 3A (IV=0.25 to 0.43 dL/g), and 5050DL 4A (IV=0.38 to 0.48 dL/g), which are copolymers provided by Lakeshore Biomaterials Company (formerly Alkermes Company), USA, having a lactide:glycolide ratio of 1:1; and the like.

In another aspect, the biodegradable polymer may be a polymer-sugar complex wherein a sugar is coupled with a polymer selected from the group consisting of polylactides (PLA), polyglycolides (PGA), poly(lactide-co-glycolide)s (PLGA), polyorthoesters, polyanhydrides, polyhydroxybutyric acids, polycaprolactones, and polyalkylcarbonates, a copolymer of at least two of the polymer group, or a copolymer of polyethylenglycol (PEG) and one of the polymer group.

In an embodiment of the present invention, the polymer-sugar complex may refer to a complex wherein the polymer is substituted for a hydroxyl group of the sugar. The sugar may include monosaccharides and polysaccharides which include 1 to 8 saccharide units, wherein each saccharide unit includes 3 to 6 hydroxyl groups, and straight chain sugar-alcohols including 3 to 6 hydroxyl groups and having a molecular weight of 20,000 or less. The sugar-alcohols may include mannitol, pentaerythritol, sorbitol, ribitol, and xylitol. The polymer couples with the sugar at three or more hydroxyl groups present in the sugar.

The polymer-sugar complex according to the above embodiment has in vivo properties similar to the polymer that is coupled with sugar, has various degradation rates depending on the kind of the polymer used, and is degraded to a harmless polymer and sugar in the body, and therefore it may be suitable for the biodegradable polymer. In a preferable embodiment, the polymer-sugar complex may be a PLA-glucose complex, a PGA-glucose complex, or a PLGA- glucose complex, wherein the PLGA-glucose complex may be one having the following structure:

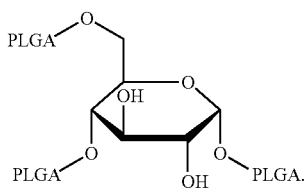

In the controlled-release microspheres according to the present invention, the coating layer formed on the surface thereof allows effective control of the initial burst of exendin, thereby preventing the side effects caused by the excessive initial burst. The biodegradable polymer may be used without any limitation of viscosity.

In the controlled-release composition according to the present invention, the biodegradable polymer plays a role as a matrix for preserving the active ingredient, the exendin, where an insufficiently low viscosity of the polymer fails to effectively preserve the active ingredient, thereby increasing the initial burst, and an excessively high viscosity of the polymer causes a decrease in the total released amount of the active ingredient, thereby decreasing the bioavailability thereof. In the present invention, not only the biodegradable polymer but also the coating materials contained in the composition play a role of controlling drug release, and thus the biodegradable polymer having a relatively low viscosity can be used. Therefore, in order to effectively control the initial burst of drug and improve the bioavailability, the intrinsic viscosity (IV) of the biodegradable polymer, which is measured for a biodegradable polymer dissolved in chloroform at a concentration of 1% (W/V) at 25° C.±0.1° C. using a Ubbelohde Viscometer, may preferably be 0.1 to 0.6 dL/g, more preferably 0.15 to 0.31 dL/g, and even more preferably 0.16 to 0.24 dL/g.

In the composition, or the microspheres of the present invention, the biodegradable polymer plays a role as a matrix for preserving the active ingredient during release and controlling the release rate, where its content in the composition or the microspheres may preferably be 85 to 99.89 parts by weight, and more preferably 91 to 99 parts by weight, based on 100 parts by weight of the composition or the microspheres containing the exendin, biodegradable polymer(s), and coating material(s).

The coating material is used for preventing excessive release and increasing the bioavailability of the active ingredient, and in the microspheres of the present invention, it may be in the form of a coating layer on the surface thereof. The coating material may be one or more selected from basic amino acids, polypeptides, and organic nitrogen compounds. The basic amino acid may include arginine, lysine, histidine, and their derivatives. The polypeptide may include 2 to 10 amino acids, and more preferably 2 to 5 amino acids, including one or more selected from arginine, lysine, and histidine. The polypeptide may include more basic amino acids than acidic amino acids, thereby exhibiting a basic property. For example, the polypeptide may be L-Ala-L-His-L-Lys, L-Arg-L-Phe, Gly-L-His, Gly-L-His-Gly, Gly-L-His-L-Lys, L-His-Gly, L-His-Leu, L-Lys-L-Tyr-L-Lys, L-His-L-Val, L-Lys-L-Lys, L-Lys-L-Lys-L-Lys, L-Lys-L-Thr-L-Thr-L-Lys-L-Ser, and the like. Further, the organic nitrogen compound may be creatine, creatinine, urea, and the like.

The content of the coating material contained in the composition of the present invention, or coated on the microspheres, may preferably be 0.01 to 5 parts by weight, and more preferably 0.015 to 3 parts by weight, based on 100 parts by weight of the composition or the microspheres containing exendin, biodegradable polymer(s), and coating material(s). An effective control of drug release cannot be obtained if the content of the coating material is lower than the above scope, whereas the effect of controlling the initial burst is not additionally increased even if the content of the coating material is increased to higher than the above scope. Thus, the above scope of the content of the coating material may be preferred.

Each controlled-release microsphere according to the present invention has a smooth surface coated with the coating material, and an average size of 1 to 50 µm, and preferably 5 to 30 µm (see FIG. 4-b). Such smooth surface of the microsphere allows achievement of effective initial burst control and excellent bioavailability.

Unlike the conventional form, the controlled-release microsphere or a microsphere prepared from the composition of the present invention is coated with the coating material, allowing prevention of an excessive initial burst and an increase in bioavailability, which cannot be obtained in the conventional exendin-containing microsphere. In particular, an excessive initial burst of exendin causes various side effects, such as vomiting, nausea, headache, and the like, and thus it is very important to lower the initial burst amount to 5% or below. The controlled-release microsphere or a microsphere prepared from the composition of the present invention allowing lowering the released amount for the initial 24 hours to 5% or below. In order to decrease the side effects due to administering exendin-containing controlled-release microsphere, the initial burst amount for the initial hour may preferably be 5% or below, and more preferably 1% or below, as measured by an in vitro release test described herein.

There have been various attempts to lower the side effects due to the excessive initial burst of exendin-containing microspheres prepared by conventional methods. However, most of such attempts that achieve successful prevention of the excessive initial burst have some problems in that the total release as well as the initial burst is decreased, thereby considerably decreasing the bioavailability of the drug. However, the microspheres of the present invention contain a coating layer of the coating material on the surface thereof, allowing effective control of the initial burst to remove the side effects due to the excessive initial burst, and obtain a lasting and sufficient release of drug to achieve excellent bioavailability.

In an embodiment of the present invention, the composition or the microspheres may additionally contain excipients such as protective colloids and/or stabilizers.

The composition or the microspheres may additionally contain one or more protective colloids selected from polyvinyl alcohols, albumins, polyvinylpyrrolidones, gelatins, and the like. Although the protective colloid has no special effect to prevent the excessive initial burst of exendin contained in the microspheres, it plays a role to prevent aggregation between the microspheres and improve dispersibility. Considering such role, the content of the protective colloid may preferably be 0.02% (W/W) to 1.0% (W/W), based on the weight of the composition or the microspheres containing the exendin, biodegradable polymer(s), and coating material(s).

In addition, in order to improve the stability of the microspheres during freeze-drying, the composition or the microspheres of the present invention may additionally contain excipients selected from mannitol, trehalose, sucrose, sodium carboxymethyl cellulose, and the like, in an amount of 5% (W/W) to 30% (W/W), and more preferably 10% (W/W) to 20% (W/W), based on the weight of the composition or the microspheres containing the exendin, biodegradable polymer(s), and coating material(s).

Further, the composition or the microsphere of the present invention may additionally contain any additives and excipients conventionally used in drug formulation, the kind and the content of which may be easily determined by one skilled in the relevant art.

In another aspect, the present invention provides a method of preparing the exendin-containing controlled-release microspheres as described above. The exendin-containing controlled-release microspheres according to the present invention may be prepared by various methods, for example by coating the surface of the microspheres through suspending the microspheres in the coating material solution during or after the preparation of the microspheres, to prepare the controlled-release microspheres. The method of preparing the microspheres according to the present invention may be performed by a double emulsion method (W/O/W method), single emulsion method (O/W method), a phase-separation method, a spray drying method, and the like.

Specifically, the method of preparing the exendin-containing controlled-release microspheres may include the steps of:
mixing exendin and biodegradable polymer(s) to prepare a W/O-type emulsion or a homogeneous mixture; and
emulsifying by adding the emulsion or the homogeneous mixture into an aqueous solution of a coating material to form a coating layer.

More specifically, in the case of using a double emulsion method, the method of the present invention may include the steps of emulsifying by mixing an exendin aqueous solution and a biodegradable polymer dissolved in an organic solvent to form a primary emulsion (W/O-type); suspending the emulsion in an aqueous solution of a coating material to form a W/O/W-type emulsion; heating the W/O/W-type emulsion to remove the solvent and harden the obtained microspheres; collecting and washing the hardened microspheres; and freeze-drying the microspheres. The organic solvent may be any organic solvent that is capable of forming an emulsion by dissolving the biodegradable polymer and then being mixed with an aqueous solution, and, for example, it may be one or more selected from the group consisting of chloroform, ethylacetate, methylenechloride, and methylethylketone, and is preferably methylenechloride. In this case, the coating material is contained in a secondary aqueous phase (outer aqueous phase of the W/O/W emulsion), to form a coating layer on the outside of the microspheres containing exendin and the biodegradable polymer, when the organic solvent is removed.

Alternatively, if a single emulsion method is employed, the method of the present invention may include the steps of dissolving the exendin and a biodegradable polymer in an organic solvent to form a homogeneous mixture; adding an aqueous solution containing a coating material to the obtained mixture to form an emulsion; heating the emulsion to remove the solvent and harden the obtained microspheres; collecting and washing the hardened microspheres; and freeze-drying the microspheres. The organic solvent may be any organic solvent that is capable of completely mixing the exendin and the biodegradable polymer to form a homogeneous mixture, and of being mixed with an aqueous solution to form an emulsion. For example, the organic solvent may be a mixed solvent wherein one or more selected from the group consisting of alcohols having 1 to 5 carbon atoms, glacial acetic acid, formic acid, dimethyl sulfoxide, and n-methylpyrrolidone, and one or more selected from the group consisting of chloroform, ethyl acetate, methylethylketone, and methylene chloride are mixed, and preferably, wherein methanol and methylene chloride are mixed. In this case, the surface the finally-obtained microspheres has a coating layer thereon, by emulsifying the homogeneous mixture of the biodegradable polymer and the exendin and adding the coating material to an aqueous solution for removing the organic solvent.

In another aspect, the method of preparing exendin-containing controlled-release microspheres according to the present invention may include the steps of:
mixing the exendin and a biodegradable polymer to form an emulsion or a homogeneous mixture;
solidifying the obtained emulsion or homogeneous mixture to prepare primary microspheres; and suspending the obtained primary microspheres in an aqueous solution of a coating material to form a coating layer on each microsphere.

The solidifying method has no limitation, and may be any solidifying method conventionally used in the relevant art, for example a phase-separation method or a spray drying method.

More specifically, if a phase-separation method is employed in the solidifying step, the method of the present invention may include the steps of:

mixing an exendin aqueous solution and a biodegradable polymer dissolved in an organic solvent to form an emulsion, or mixing the exendin and a biodegradable polymer in a mixed solvent to form a homogeneous mixture solution;

adding an oil, such as silicon oil, to the obtained emulsion or solution to prepare primary microspheres;

adding a non-solvent for the biodegradable polymer, such as a mixed solvent of an alcohol having 1 to 5 carbon atoms and an alkane having 1 to 12 carbon atoms, preferably a mixed solvent of ethanol and heptane, to remove the organic solvent from the microspheres and harden the microspheres;

suspending the obtained microspheres in an aqueous solution of a coating material to form a coating layer on each microsphere; and collecting, washing, and freeze-drying the coating layer-formed microspheres.

The organic solvent may be one or more selected from the group consisting of chloroform, ethyl acetate, methylene chloride, and methylethylketone, and preferably it may be methylene chloride. The mixed solvent may be one wherein one or more selected from the group consisting of an alcohol having 1 to 5 carbon atoms, glacial acetic acid, formic acid, dimethyl sulfoxide, and n-methylpyrrolidone, and one or more selected from the group consisting of chloroform, ethyl acetate, methylethylketone, and methylene chloride, are mixed, and preferably it may be a mixed solvent of methanol and methylene chloride.

Alternatively, if a spray drying method is employed, the method of the present invention may include the steps of:

mixing an exendin aqueous solution and a biodegradable polymer dissolved in an organic solvent to form an emulsion, or mixing exendin and a biodegradable polymer in a single solvent or a mixed solvent to form a homogeneous mixture solution;

spray-drying the obtained emulsion or solution to prepare primary microspheres;

suspending the obtained primary microspheres in an aqueous solution of a coating material to form a coating layer on each microsphere; and washing and freeze-drying the coating layer-formed microspheres.

The organic solvent may be one or more selected from the group consisting of chloroform, ethyl acetate, methylene chloride, and methylethylketone, and it may preferably be methylene chloride. The single solvent may be one or more selected from the group consisting of glacial acetic acid and formic acid, and the mixed solvent may be one wherein one or more selected from the group consisting of an alcohol having 1 to 5 carbon atoms, glacial acetic acid, formic acid, dimethyl sulfoxide, and n-methylpyrrolidone, and one or more selected from the group consisting of chloroform, ethyl acetate, methylethylketone, and methylene chloride, are mixed, and is preferably a mixed solvent of methanol and methylene chloride.

The method of the present invention may further include a step of adding a protective colloid material through any conventional method, and preferably, protective colloid material may be added during the step of coating the microspheres with the coating material.

The preferable concentration of the coating material dissolved in aqueous phase or in aqueous solution may be from 0.01 M to 1 M, and preferably from 0.1 M to 0.5 M. A lower concentration of the coating material than the above scope fails to completely coat the surface of the microspheres with the coating material, whereas a higher concentration of the coating material than the above scope results in a supersaturated coating material solution, which cannot result in an improved effect on controlling the initial burst, and thus the concentration of the coating material may be preferably within the above scope.

In the method of the present invention, the kinds and the contents of exendin, the biodegradable polymers, and the coating materials are as described above.

The exendin-containing composition of the present invention may be administered through an oral or parenteral pathway, and preferably a parenteral pathway, such as an intravenous pathway, a subcutaneous pathway, an intramuscular pathway, an intraperitoneal pathway, and the like. Therefore, in a preferable embodiment of the present invention, the exendin-containing composition may be applied as an injection solution in the form of a dispersed solution. The effective amount of the composition may be suitably adjusted according to the age of the subject, the kind and the seriousness of the disease, and the condition of the subject, and the dosage of the active ingredient in the composition may be from 0.01 to 100 μg/kg/day, and more preferably from 0.1 to 10 μg/kg/day, which may be administered at once or dividedly at several times.

The present invention is further explained in more detail with reference to the following examples. These examples, however, should not be interpreted as limiting the scope of the present invention in any manner.

EXAMPLE 1

Example 1

Preparation of Exendin-4 Containing Microspheres by a Spray Drying Method 4.850 g of a biodegradable polymer, RG502H (Lot No. 1009848, IV=0.19 dL/g), and 0.150 g of exendin-4 (Polypeptide Laboratories, USA) were homogeneously dissolved in 97 mL of glacial acetic acid 97 mL. The prepared solution was supplied into a spray dryer (SODEVA, France) equipped with an ultrasonic nozzle (Sono-tek, 120 kHz) at a flow rate of 1.5 mL/min using a piston pump, while supplying dried air at 180° C., to prepare microspheres. The prepared microspheres were suspended in a 0.5 M lysine aqueous solution (Formulation 1-1), a 0.01 M lysine aqueous solution (Formulation 1-2), a 0.1 M histidine aqueous solution (Formulation 1-3), and a 0.5 M arginine aqueous solution (Formulation 1-4), respectively, where the solutions contain 1% (W/V) polyvinyl alcohol (polyvinyl alcohol, Gohsenol, EG-50) as a protective colloid, stirred for three hours, collected, washed with distilled water, and then freeze-dried. For comparison, the same suspending, stirring, washing, and freeze-drying steps were performed except using 1% (W/V) polyvinyl alcohol aqueous solution without coating materials (Formulation 1).

Example 2

Effects of the Composition Depending on the Polymer

Exendin-4 containing microspheres were prepared by the same method as in Example 1, except for using RG503H (Lot No. 1006370, IV=0.38 dL/g, Formulations 2, 2-1 and 2-2), a mixture of the same amount of RG502H and RG503H (Lot No. 1009848:Lot No. 1006370=1:1, IV=0.29 dL/g, Formulations 3 and 3-1), RG504H (Lot No. 1016605, IV=0.51 dL/g, Formulations 4 and 4-1), 5050DL 2A (Lot No. LP-207, IV=0.18 dL/g, Formulations 5 and 5-1), and 5050DL 4A (Lot No. LP-206, IV=0.46 dL/g, Formulations 6 and 6-1), as a biodegradable polymer.

Experimental Example 1-1

Testing the Effects of Microsphere Coating

The content of exendin contained in the microspheres prepared in Examples 1 and 2 was quantified by the following method. Exendin-4 (Polypeptide Laboratories, USA) was dissolved in DMSO (Dimethylsulfoxide), diluted by DMSO to the concentration as 2, 5, and 10 µg/mL, respectively, which were used as standard solutions, and subjected to fluorescence measurement at Ex 280 nm, and Em 350 nm using a fluorescence spectrometer (Cary Eclipse, Varian, USA) to obtain a measurement line. The prepared microspheres were dissolved in DMSO to the concentration of 150 µg/mL, and then the fluorescence measured therefrom was extrapolated in the measurement line, thereby determining the content of exendin in the microspheres.

A fluorescamine quantification method was used for determining the content of the coating materials used in the composition of the present invention, and in particular, lysine, arginine, histidine, and the like contained in the surface of the microspheres. A solution where the obtained microspheres are dissolved in DMSO to the concentration of 150 µg/mL was mixed with 0.01% (W/V) fluorescamine acetone solution and 0.5M sodium borate solution (pH 9.5), incubated at room temperature for 20 minutes, and subjected to a fluorescence measurement at Ex 392 nm and Em 480 nm using a fluorescence spectrometer (Cary Eclipse, Varian, USA). Using the same method, the used coating materials were dissolved in DMSO and diluted with DMSO to the concentrations of 2, 5, and 10 µg/mL, respectively, to prepare standard solutions. Thereafter, a fluorescence measurement was conducted to obtain a measurement line, thereby quantifying the coating materials in the surface of the microspheres.

In order to confirm the initial burst inhibiting effect by the microspheres, the in vitro released amounts from the microspheres coated with the coating material and the existing microspheres without coating were measured. 10 mg of each of the microspheres were suspended in 1 mL of a release test solution (10 mM HEPES, pH 7.5, 100 mM NaCl), and incubated at 37° C. while revolving at 5 rpm. After 1 and 24 hours, each sample was collected and centrifuged. The released amount of exendin in the supernatant was determined by a fluorescence measurement at Ex 280 nm and Em 350 nm.

The content and in vitro initial burst of the microspheres prepared in this example was examined as described above, and the obtained results are summarized in the following Table 1. Table 1 shows decrease the in vitro initial burst depending on the kinds of the coating materials and the biodegradable polymers.

TABLE 1

| Formulation No. | Polymer | Suspension | TL (%) | DC (%) | Surface content of basic organic materials (%) | 1 h release (%) | 24 h release (%) |
|---|---|---|---|---|---|---|---|
| 1 | 502H | 1% PVA | 3 | 2.76 | — | 4.50 | 9.90 |
| 1-1 | 502H | 1% PVA + 0.5 M lys | 3 | 2.73 | 0.249 | 0.79 | 3.84 |
| 1-2 | 502H | 1% PVA + 0.01 M lys | 3 | 2.72 | 0.099 | 3.76 | 5.66 |
| 1-3 | 502H | 1% PVA + 0.1 M his | 3 | 2.71 | 0.015 | 1.53 | 3.51 |
| 1-4 | 502H | 1% PVA + 0.5 M arg | 3 | 2.56 | 0.156 | 1.46 | 4.60 |
| 2 | 503H | 1% PVA | 3 | 2.88 | — | 1.40 | 1.50 |
| 2-1 | 503H | 1% PVA + 0.5 M lys | 3 | 2.96 | 0.057 | 0.00 | 0.29 |
| 2-2 | 503H | 1% PVA + 0.1 M his | 3 | 2.85 | 0.132 | 0.00 | 0.58 |
| 3 | 502H:503H | 1% PVA | 3 | 2.75 | — | 2.80 | 4.00 |
| 3-1 | 502H:503H | 1% PVA + 0.5 M lys | 3 | 2.91 | 0.056 | 0.00 | 0.75 |
| 4 | 504H | 1% PVA | 3 | 2.46 | — | 1.23 | 2.25 |
| 4-1 | 504H | 1% PVA + 0.5 M lys | 3 | 2.47 | 0.018 | 0.81 | 0.84 |
| 5 | 5050DL 2A | 1% PVA | 3 | 2.53 | — | 1.31 | 1.95 |
| 5-1 | 5050DL 2A | 1% PVA + 0.5 M lys | 3 | 2.54 | 0.034 | 1.02 | 1.66 |
| 6 | 5050DL 4A | 1% PVA | 3 | 2.40 | — | 1.21 | 2.03 |
| 6-1 | 5050DL 4A | 1% PVA + 0.5 M lys | 3 | 2.51 | 0.018 | 0.79 | 0.82 |

* TL (%): Target loading %
DC (%): Actual drug content %

As shown in Table 1, it is revealed that the released amounts of the formulations coated with the coating materials according to the present invention for the initial hour and at 24 hours are decreased compared with those of formulations 1, 2, 3, 4, 5, and 6 that are merely suspended in a protective colloid, polyvinyl alcohol solution, after spray drying. Such effects are obtained regardless of the viscosity range of the polymer, and are important in preventing the side effects caused by a sudden increase of the initial blood concentration immediately after administration of the exendin-containing controlled-release microspheres.

Experimental Example 1-2

Decrease in Blood Drug Concentration During Initial Stage after Administration According to Viscosity of Polymers and Coating Materials Since the side effects of exendins are caused by a sudden increase in the blood drug concentration at the initial stage after administration, it is very important to prevent the blood drug concentration increase by initial drug release directly after administration. It has been revealed that the blood drug concentrations of the formulations according to the present invention reach a peak concentration during the hour after administration and then decline. In order to determine the bioavailability and the peak of the initial blood concentration (Conc. 1h) of the formulations prepared by Examples 1 and 2 after administration, the formulations were administered into male S.D. rats (350±20 g). The exendin-containing microspheres prepared as above were suspended in a medium (0.5% (W/W) sodium carboxymethyl cellulose, 5% (W/W) mannitol, and 0.1% (W/W) Tween 80), and then subcutaneously injected at a dose of 0.6 mg (exendin)/kg after anesthetizing with ether. Blood was collected through the tail vein at time 0 and at the end of the $1^{st}$ hour, and at the $1^{st}$, $2^{nd}$, $4^{th}$, $7^{th}$, $14^{th}$, $21^{st}$, and $28^{th}$ day after administration, and centrifuged at 12,000 rpm at 4° C. for 10 minutes. Then, serum collected therefrom and stored at −20° C. Exendin in the serum was quantified by using an enzyme-immunoassay kit (EK-070-94, Phoenix Pharmaceuticals, Inc., USA), and the relative bioavailability was compared by the area under a curve (AUC) of the obtained time-blood concentration curve.

Figure 2:
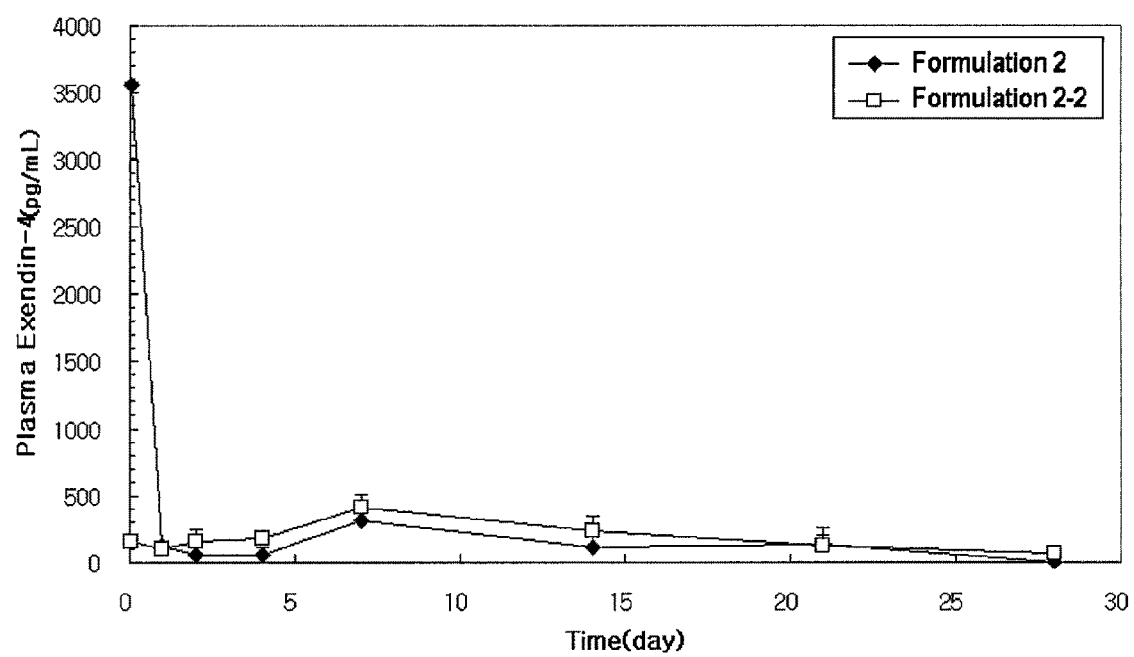
FIG. 2 is a graph showing a change in blood drug concentration in rats depending on the presence of a coating layer in an exendin-containing formulation of RG503H.
Figure 3:
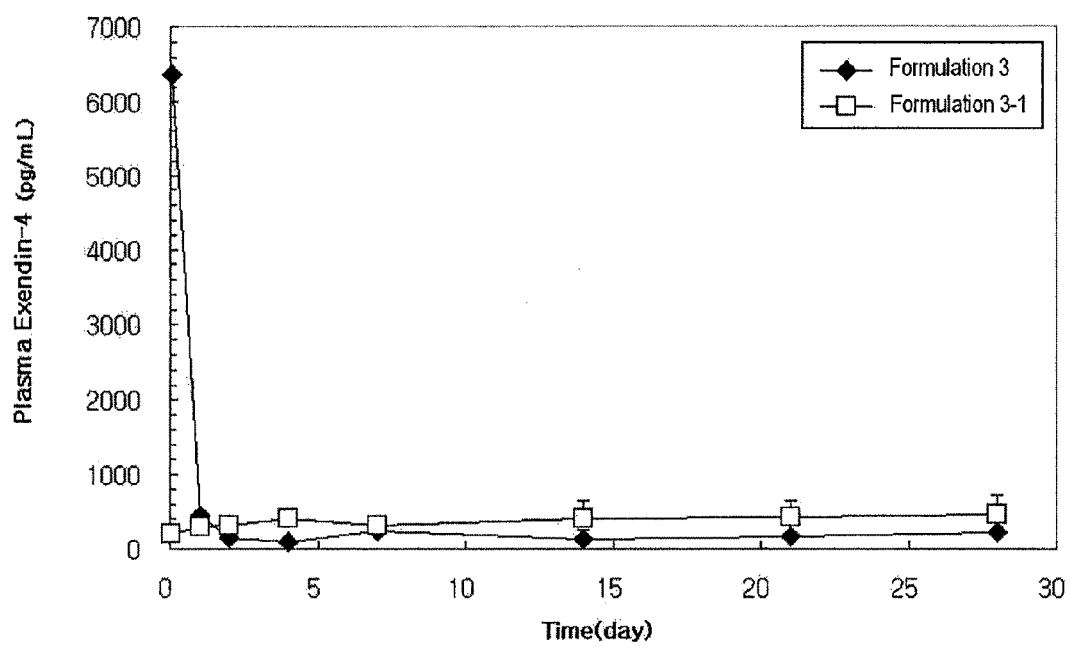
FIG. 3 is a graph showing a change in blood drug concentration in rats depending on the presence of a coating layer and the kind of coating materials in an exendin-containing formulation mixture of RG502H:RG503H=1:1.

The obtained blood concentration graphs are shown in FIGS. 1 to 3, and the obtained results are summarized in Table 2. Table 2 shows the results of decrease in blood drug concentration at the initial stage after administration and AUC comparison according to coating materials and polymer viscosity.

TABLE 2

| Formulation No. | Polymer | Suspension | DC (%) | Conc. 1 h | AUC |
|---|---|---|---|---|---|
| 1 | 502H | 1% PVA | 2.76 | 10969 (1 h) | 24169 |
| 1-1 | 502H | 1% PVA + 0.5 M lys | 2.73 | 900 (1 h) | 26681 |
| 2 | 503H | 1% PVA | 2.88 | 3561 (1 h) | 5401 |
| 2-1 | 503H | 1% PVA + 0.5 M lys | 2.96 | 159 (1 h) | 5569 |
| 3 | 502H:503H | 1% PVA | 2.75 | 6363 (1 h) | 8030 |
| 3-1 | 502H:503H | 1% PVA + 0.5 M lys | 2.91 | 320 (1 h) | 10909 |

* DC (%): Actual drug Content w %
AUC: Area Under the Curve (pg * day/mL)

As shown in FIGS. 1 to 3 and Table 2, it is revealed that the non-coated formulations exhibit higher peak blood concentration at the initial stage after administration than the coated formulations. In addition, it is also revealed that the polymer RG502H having the lowest viscosity exhibited the highest AUC value, i.e., the highest bioavailability, and that the coating with the coating materials allows improvement of the bioavailability of the formulations with high molecular weight polymers as well as the formulations with low molecular weight polymers. In conclusion, although the bioavailability depends on the viscosity of the polymer used, the effective inhibition of initial burst, which cannot be achieved in the existing formulations prepared by the conventional methods, can be achieved by coating with the coating materials according to the present invention.

Example 3

Preparation of Microspheres with Various Drug Loadings

The biodegradable polymer RG502H and exendin-4 were mixed so as to make the content of exendin-4 1% (w/w) (Formulations 7 and 7-1) and 7% (w/w) (Formulations 8 and 8-1), respectively, and the mixtures were dissolved in glacial acetic acid. The obtained solutions were spray dried by the same method as in Example 1 to prepare microspheres. The prepared microspheres were suspended in a 1% polyvinyl alcohol aqueous solution (Formulations 7 and 8), and a 1% polyvinyl alcohol, 0.5 M lysine aqueous solution (Formulations 7-1 and 8-1), respectively, for three hours, and were collected, washed with distilled water, and freeze-dried.

Experimental Example 2

Initial Burst Decrease Depending on Various Drug Loadings

The initial burst of the microspheres prepared in Example 3 was quantified by the same method as in Experimental Example 1-1, and the obtained results are summarized in Table 3. Table 3 shows the coating effect with the coating materials depending on the drug contents.

| Formulation No. | TL (%) | DC (%) | Surface content of basic organic materials (%) | 1 h release (%) | 24 h release (%) |
|---|---|---|---|---|---|
| 7 | 1 | 0.85 | — | 3.06 | 3.87 |
| 7-1 | 1 | 0.81 | 0.295 | 2.63 | 3.68 |
| 1 | 3 | 2.76 | — | 4.50 | 9.90 |
| 1-1 | 3 | 2.73 | 0.249 | 0.79 | 3.84 |
| 8 | 7 | 5.79 | — | 8.00 | 11.34 |
| 8-1 | 7 | 5.85 | 1.636 | 2.04 | 5.47 |

As shown in Table 3, Formulations 1, 7, and 8 that are not coated with the coating materials exhibit increased initial burst according to an increase of the amount of exendin loaded in the biodegradable polymer, whereas Formulations 1-1, 7-1, and 8-1 that are coated with the coating materials exhibit considerably decreased initial burst regardless of the amount of exendin loaded in the biodegradable polymer.

Example 4

Preparation of Exendin-4 Containing Microspheres by a Double Emulsion Method 970 mg of RG502H was dissolved in 3.23 mL of dichloromethane (Junsei Chem.). 30 mg of exendin-4 dissolved in 0.3 mL of distilled water was added to the obtained RG502H solution and sonicated to prepare a primary W/O emulsion. The obtained emulsion was injected to 270 mL of 0.5% (w/v) polyvinyl alcohol aqueous solution while stirring at 5000 rpm to prepare a W/O/W emulsion. The emulsion was suspended at 4000 rpm at 40° C. for one hour, thereby removing dichloromethane and hardening the polymer, and then the obtained microspheres were collected. The collected microspheres were washed twice with distilled water and subjected to freeze-drying to prepare microspheres. In preparing formulations by the same method as above, the suspension for injecting the primary emulsion was suspended in 1% PVA (Formulation 9), 0.5 M lysine aqueous solution +1% PVA (Formulation 9-1), 0.5 M Tris aqueous solution +1% PVA (Formulation 9-2), 0.5 M urea aqueous solution +1% PVA (Formulation 9-3), 0.05 M creatinine aqueous solution +1% PVA (Formulation 9-4), 0.5 M creatine aqueous solution +1% PVA (Formulation 9-5), respectively, for one hour, and collected, washed with distilled water, and subjected to freeze-drying.

Figure 4A:
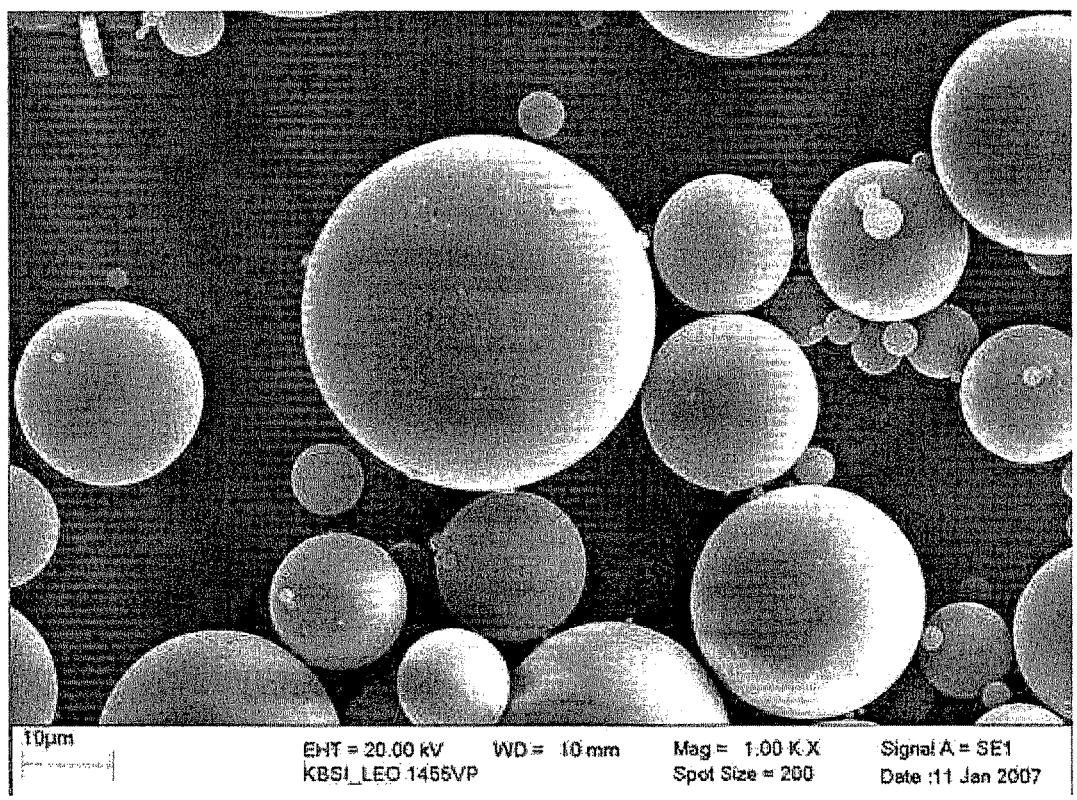
FIG. 4a is an electron microscope image of microspheres prepared by a conventional double emulsion method.
Figure 4B:
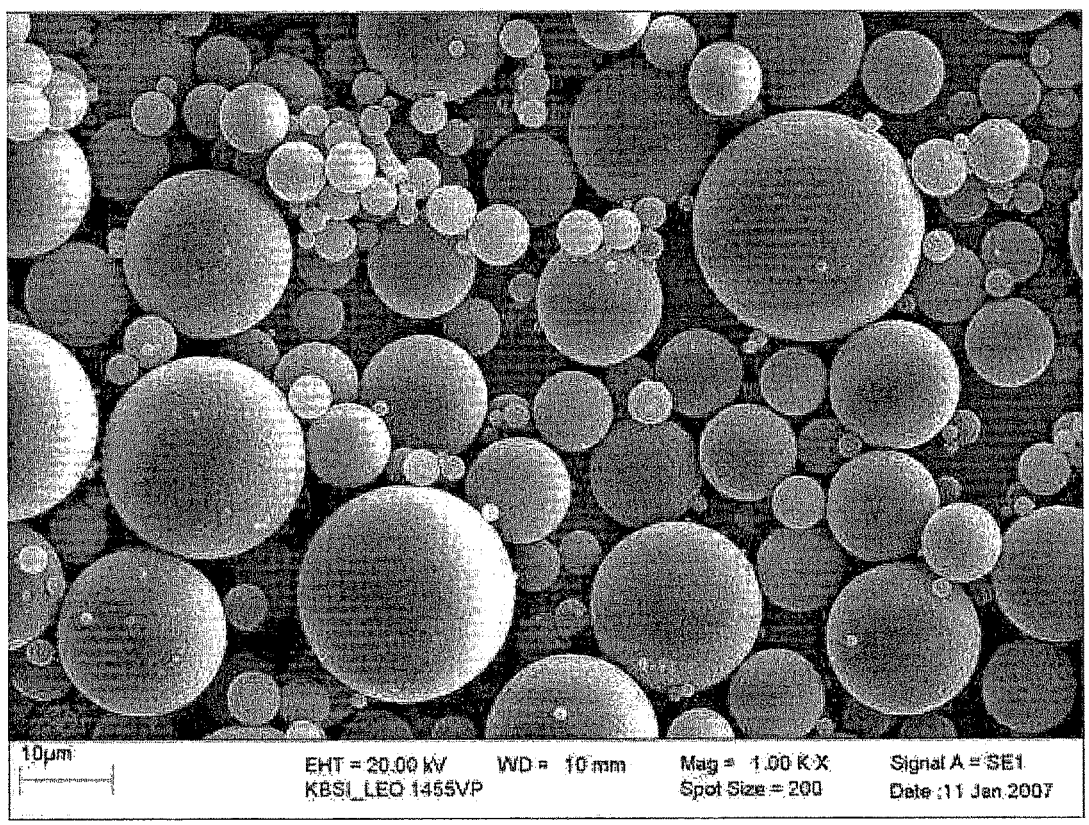
FIG. 4b is an electron microscope image of microspheres coated with specific coating materials by a double emulsion method according to the present invention.

The electron microscopic images of the obtained microspheres as above are shown in FIGS. 4a and 4b. FIG. 4a shows Formulation 9 that is not coated with the coating material, and FIG. 4b shows Formulation 9-1 that is coated with the coating material. As shown in FIG. 4b, it is revealed that the formulation according to the present invention has a smooth surface.

Experimental Example 3

Decrease in Initial Burst Depending on the Kind of Coating Material

The drug release of the microspheres obtained in Example 4 during the initial 24 hours after administration were quantified by the same method as in Experimental Example 1-1, and the obtained results are summarized in Table 4. Table 4 shows the decreased initial burst depending on the coating material.

TABLE 4

| Formulation No. | Suspension | 1 h release (%) | 24 h release (%) |
|---|---|---|---|
| 9 | 1% PVA | 7.45 | 13.88 |
| 9-1 | 1% PVA + 0.5 M lys | 0.87 | 1.87 |
| 9-2 | 1% PVA + 0.5 M tris | 5.79 | 9.91 |
| 9-3 | 1% PVA + 0.5 M urea | 2.23 | 5.04 |
| 9-4 | 1% PVA + 0.05 M creatinine | 2.20 | 3.06 |
| 9-5 | 1% PVA + 0.5 M creatine | 0.89 | 1.23 |

As shown in Table 4, although the decreased amount of initial burst slightly varies depending on the kind of coating material used, microsphere Formulations 9-1 to 9-5 coated with the coating materials exhibit considerably decreased initial burst compared with microsphere Formulation 9 that is not coated with the coating materials.

Comparative Example

Preparation of Microspheres Loaded with Exendin-4 and Coating Materials, and Measurement of Initial Burst 970 mg of RG502H was dissolved in 3.23 mL of dichloromethane (Junsei Chem.). 30 mg of exendin-4 and 6.68 mg of lysine were dissolved in 0.3 mL of distilled water and added to the obtained RG502H solution to prepare a primary W/O emulsion. The obtained emulsion was suspended in a 1% PVA aqueous solution, and microsphere Formulation 10 was prepared by the same method as in Example 4. In addition, 970 mg of RG502H and 6.68 mg of lysine were dissolved in 3.23 mL of dichloromethane (Junsei Chem.). To the obtained solution, 30 mg of exendin-4 dissolved in 0.3 mL of distilled water was added, to prepare a primary W/O emulsion. The emulsion was suspended in a 1% PVA aqueous solution to prepare microsphere Formulation 11.

Figure 4C:
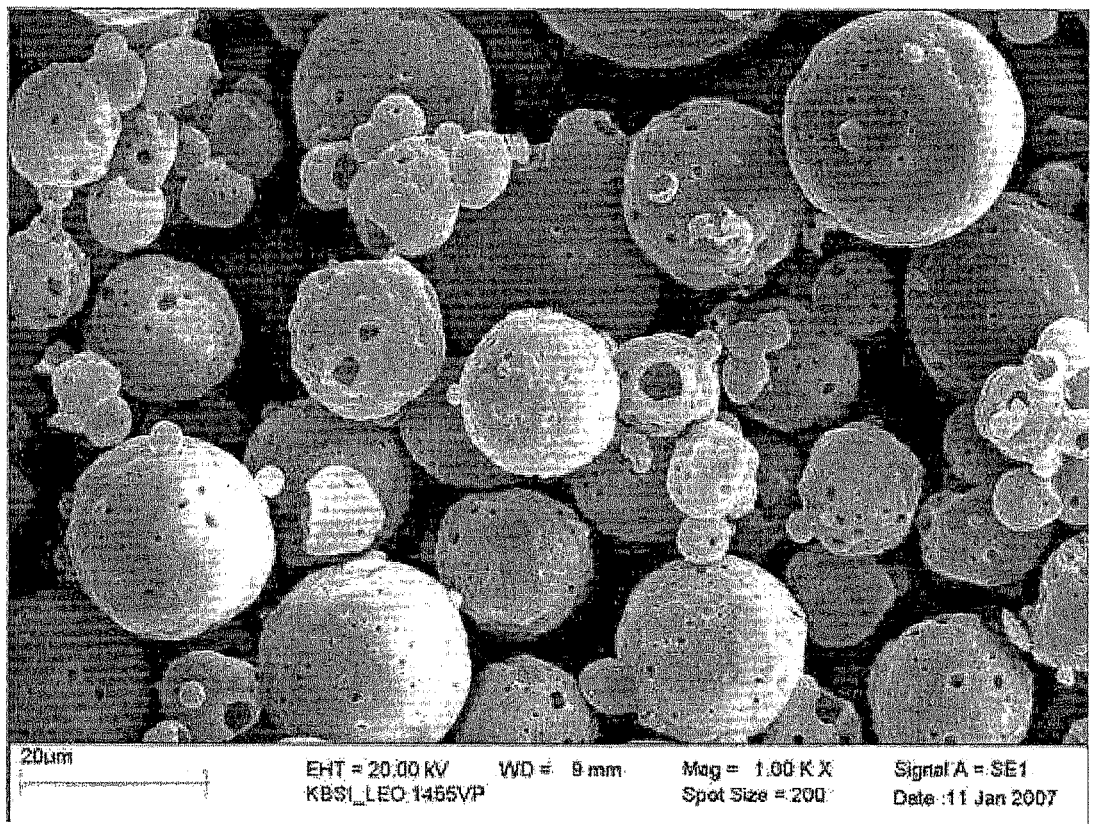
FIG. 4c is an electron microscope image of microspheres prepared by a double emulsion method with coating materials in primary aqueous phase.
Figure 4D:
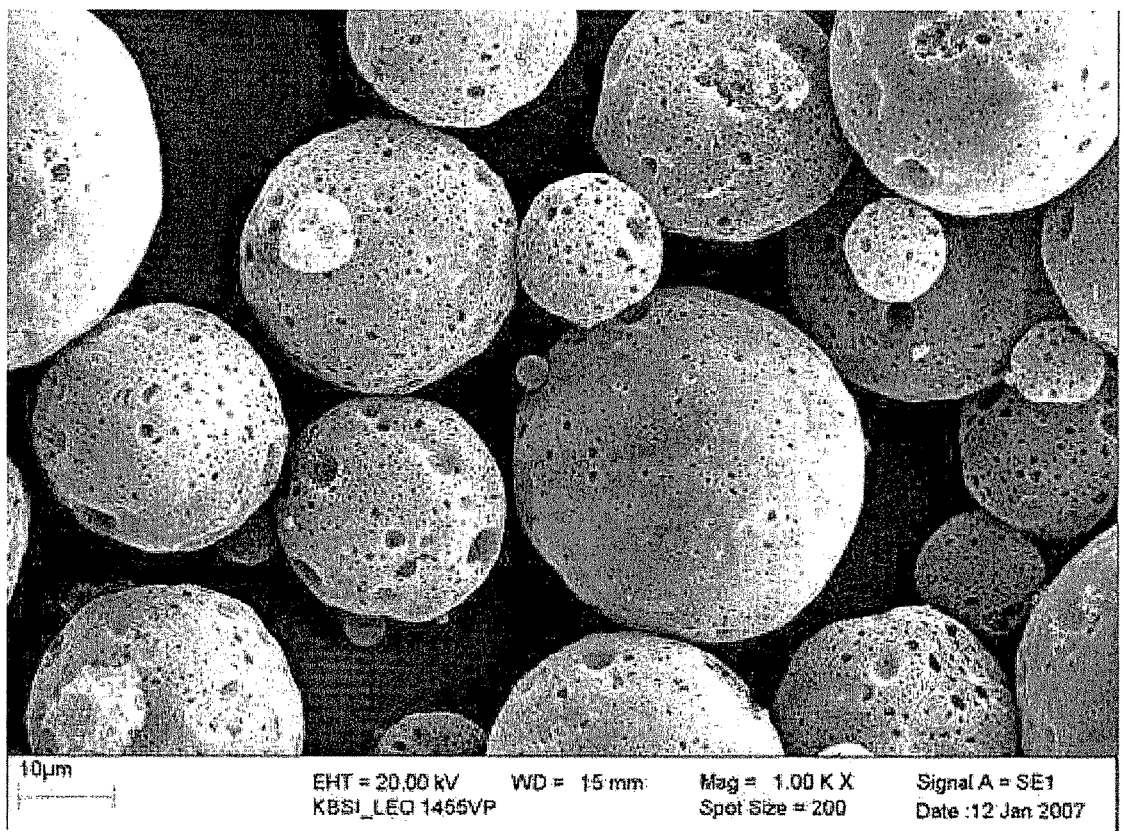
FIG. 4d is an electron microscope image of microspheres prepared by a double emulsion method with coating materials dissolved with oil phase polymers.

Electron microscopic images of the above-prepared Formulations 10 and 11 are shown in FIGS. 4c and 4d. As shown in FIG. 4c, the microspheres prepared in the comparative example have many pores on their surfaces.

The released amounts of the microspheres prepared in the comparative example for the initial 1 and 24 hours were respectively measured by the same method as in Experimental Example 1-1, and the obtained results are summarized in Table 5. Table 5 shows the change in the initial burst amount depending on the methods by which the coating materials are added when preparing the microspheres.

TABLE 5

| Formulation No. | Primary Emulsion | Suspension | 1 h Release (%) | 24 h Release (%) |
|---|---|---|---|---|
| 9 | 502H, exendin-4 | 1% PVA | 7.45 | 13.88 |
| 9-1 | 502H, exendin-4 | 1% PVA + 0.5 M lys | 0.87 | 1.87 |
| 10 | 502H, exendin-4 + lysine (aqueous phase) | 1% PVA | 65.63 | 71.64 |
| 11 | 502H + lysine (oil-phase), exendin-4 | 1% PVA | 80.31 | 87.00 |

As shown in Table 5, when the coating materials are simply loaded together with exendin without forming a coating layer, or are used with polymers by simply being mixed, an excessive initial burst occurs, which acts as a critical defect to prevent exendin from being formulated as a controlled-release form.

As shown in FIGS. 4c and 4d, the addition of the coating materials into either the oil-phase or the aqueous-phase of the primary emulsion causes in increase in porosity of the surface of the microspheres. In conclusion, the addition of the coating materials inside the microspheres increases the surface porosity, finally resulting in an excessive initial burst of drug contained therein. To the contrary, the microspheres coated with the coating materials according to the present invention do not have any increase in surface porosity, and they exhibit a lower initial burst than Formulation 9 having a smooth surface but not coated with the coating materials.

In conclusion, the existing exendin-containing formulations prepared by the conventional methods, for example, disclosed in Korean Patent No. 140209, cannot achieve the desired decrease of the initial burst, and thus they are not advantageously used as an efficient exendin-containing formulation due to side effects because of an excessive initial burst. To the contrary, the composition according to the present invention is very useful in developing exendin-containing controlled release microspheres that are required to have an extremely controlled initial release. In addition, the present invention can achieve high bioavailability of the exendin-containing formulation, which cannot be achieved by the conventional technique for controlling the initial burst of an exendin-containing formulation.

Example 5

Preparing Exendin-3 Containing Microspheres by a Spray Drying Method 4.850 g of a biodegradable polymer, RG502H (Lot No. 1009848, IV=0.19 dL/g), and 0.150 g of exendin-3 (Peptron Inc., South Korea), were homogeneously dissolved in 97 mL of glacial acetic acid. The obtained solution was supplied into a spray dryer (SODEVA, France) equipped with an ultrasonic nozzle (Sono-tek, 120 kHz) using a piston pump at a flow rate of 1.5 mL/min, while supplying dried air at 180° C., to prepare microspheres. The prepared microspheres were suspended in a 0.5 lysine aqueous solution supplemented with 1% (W/V) polyvinyl alcohol (polyvinyl alcohol, Gohsenol, EG-50) as a protective colloid, stirred for three hours, collected, washed with distilled water, and then freeze-dried.

Example 6

Preparation of Exendin-4(1-28)Amide Containing Microspheres by a Spray Drying Method

4.850 g of a biodegradable polymer, RG502H (Lot No. 1009848, IV=0.19 dL/g), and 0.150 g of exendin-4(1-28) amide (Peptron Inc., South Korea), were homogeneously dissolved in 97 mL of glacial acetic acid. The prepared solution was supplied into a spray dryer (SODEVA, France) equipped with an ultrasonic nozzle (Sono-tek, 120 kHz) at the flow rate of 1.5 mL/min using a piston pump, while supplying dried air at 180° C., to prepare microspheres. The prepared microspheres were suspended in a 0.5 M L-Lys-L-Thr-L-Thr-L-Lys-L-Ser aqueous solution supplemented with 1% (W/V) polyvinyl alcohol (polyvinyl alcohol, Gohsenol, EG-50) as a protective colloid, stirred for three hours, collected, washed with distilled water, suspended in 10 mL of D-mannitol 10% (W/W) aqueous solution, and then freeze-dried.

Example 7

Preparation of Exendin-4 Containing Microspheres by a Phase-Separation Method

0.1 g of exendin-4 (Polypeptide Laboratories, USA) was dissolved in 1.86 mL of distilled water, being slowly injected into a solution where 1.86 g of RG502H (Lot No. 1009848, IV=0.19 dL/g) was dissolved in 23.32 mL of dichloromethane, and sonicated, to prepare a primary emulsion. The obtained emulsion was homogenized by adding 58.8 g of silicone oil thereto, to form embryonic microspheres. A mixture of 400 g of heptane and 50 g of ethanol was slowly added to the formed embryonic microspheres while stirring at 500 rpm and maintaining the temperature of 3° C., to harden the embryonic microspheres. After stirred for approximately one hour, the solvent was removed by decantation. Then, 200 g of heptane was further added thereto, and stirred for one hour, to remove silicone oil and dichloromethane from the embryonic microspheres. The obtained microspheres were filtrated, collected, washed with heptane at 4° C., and vacuum dried, to prepare microspheres. The prepared microspheres were suspended in 0.5% (W/V) polyvinyl alcohol and a 0.5 M lysine aqueous solution for one hour, collected, washed with distilled water, and freeze-dried, to prepared a formulation.

As shown in the above examples, the present invention provides a novel exendin-containing controlled release microsphere formulation with decreased side effects and improved bioavailability, by coating the surface of the microspheres with coating materials, thereby decreasing an excessive release of the drug during the initial stage after administration.

---

What is claimed is:

1. A controlled-release microsphere with a coating layer comprising
   a core consisting essentially of an exendin as an active ingredient, and a biodegradable polymer, and
   a coating layer that coats the core and comprises 0.02 to 1.0%(w/w) PVA and one or more selected from the group consisting of arginine, lysine, histidine, creatine, creatinine, and urea as a coating material for controlling initial burst of the exendin, wherein:
   an amount of the exendin is from 0.1 to 10 parts by weight based on 100 parts by weight of the microsphere;
   an amount of the coating layer is from 0.01 to 5 parts by weight based on 100 parts by weight of the microsphere;
   the biodegradable polymer is a polymer selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate; a copolymer or a simple mixture of two or more selected the polymer group; a copolymer of the polymer and polyethyleneglycol (PEG); or a polymer-sugar complex where a sugar is coupled with the polymer or the copolymer;

the microsphere releases 5% or less than 5% of a total weight of the exendin from the microsphere in the first hour; and the exendin is one or more selected from the group consisting of exendin-3 (SEQ ID NO: 1), exendin-4 (SEQ ID NO: 2), one represented by Chemical Formula I or II, an exendin derivative having a C-terminus substituted or non-substituted with an amide group, and a pharmaceutically acceptable salt thereof:

(Chemical Formula I)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28 -Z1,

Wherein
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHε-R, wherein R is Lys, Arg, or C1-C10 straight chain or branched alkanoyl;
Xaa22 is Ala, Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
Xaa27 is Ala or Lys;
Xaa28 is Ala or Asn;
Z1 is —OH, —NH2, Gly-Z2, Gly Gly-Z2, Gly Gly Xaa31-Z2, Gly Gly Xaa31 Ser-Z2, Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2, wherein Xaa31, Xaa36, Xaa37 and Xaa38 are independently selected from the group consisting of Pro, homoproline, 3Hyp, 4Hyp, thioproline, N-alkylglycine, N-alkylpentylglycine, or N-alkylalanine, Xaa39 is Ser or Tyr, and Z2 is —OH, or —NH$_2$,
provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala; and when Xaa1 is His, Arg, or Tyr, one or more of Xaa3, Xaa4, and Xaa9 are Ala;

(Chemical Formula II)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

X1-Z1,

Wherein
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHε-R, wherein R is Lys, Arg, C1-C10 straight chain or branched alkanoyl, or cycloalleyl-alkanoyl;
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
X1 is Lys Asn, Asn Lys, Lys-NHε-R Asn, Asn Lys-NHε-R, Lys-NHε-R Ala, or Ala Lys-NHε-R, wherein R is Lys, Arg, a C1-C10 straight chain or branched alkanoyl, or cycloalkylalkanoyl;
Z1 is —OH, —NH2, Gly-Z2, Gly Gly-Z2, Gly Gly Xaa31-Z2, Gly Gly Xaa31 Ser-Z2, Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2, wherein Xaa31, Xaa36, Xaa37 and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr, and Z2 is —OH, or —NH$_2$,
provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala; and when Xaa1 is His, Arg, Tyr, or 4-imidazopropionyl, at least one of Xaa3, Xaa4, and Xaa9 is Ala.

2. The controlled-release microsphere according to claim 1, wherein the biodegradable polymer has an intrinsic viscosity of 0.1 to 0.6 dL/g.

3. The controlled-release microsphere according to claim 1, wherein the biodegradable polymer has an intrinsic viscosity of 0.15 to 0.31 dL/g.

4. The controlled-release microsphere according to claim 1, wherein the exendin derivative is a polypeptide of SEQ ID NO:3, SEQ ID NO:4, SEQ ID NO:5, or SEQ ID NO:6, having a C-terminus substituted or non-substituted with an amide group.

5. The controlled-release microsphere according to claims 1, further comprising one or more selected from the group consisting of pharmaceutically acceptable protective colloids and excipients.

6. A method of preparing an exendin-containing controlled-release microsphere with a coating layer, the method comprising the steps of:
  preparing a core by mixing an exendin and a biodegradable polymer to prepare a W/O type emulsion or a homogeneous mixture; and
  emulsifying by adding the emulsion or the homogeneous mixture to an aqueous solution comprising 0.02 to 1.0% (w/w) PVA and one or more selected from the group consisting of arginine, lysine, histidine, creatine, creatinine, and urea as a coating material for controlling initial burst of the exendin, to form a coating layer,
  wherein:
  a concentration of the aqueous solution comprising the coating material is from 0.01 M to 1 M;
  the biodegradable polymer is a polymer selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate, a copolymer or a simple mixture of two or more selected the polymer group, a copolymer of the polymer and polyethylenglycol (PEG), or a polymer-sugar complex where a sugar is coupled with the polymer or the copolymer;
  the prepared microsphere releases 5% or less than 5% of a total weight of the exendin from the microsphere in the first hour; and
  wherein the exendin is one or more selected from the group consisting of exendin-3 (SEQ ID NO: 1), exendin-4 (SEQ ID NO: 2), one represented by Chemical Formula I or II, an exendin derivative having a C-terminus substituted or non-substituted with an amide group, and a pharmaceutically acceptable salt thereof:

(Chemical Formula I)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

Xaa27 Xaa28 -Z1, wherein
  Xaa1 is His, Arg, Tyr, Ala, Norval, Val, Norleu, or 4-imidazopropionyl;
  Xaa2 is Ser, Gly, Ala, or Thr;
  Xaa3 is Ala, Asp, or Glu;
  Xaa4 is Ala, Norval, Val, Norleu, or Gly;
  Xaa5 is Ala or Thr;
  Xaa6 is Ala, Phe, Tyr, or naphthylalanine;
  Xaa7 is Thr or Ser;
  Xaa8 is Ala, Ser, or Thr;
  Xaa9 is Ala, Norval, Val, Norleu, Asp, or Glu;
  Xaa10 is Ala, Leu, Ile, Val, pentylglycine, or Met;
  Xaa11 is Ala or Ser;
  Xaa12 is Ala or Lys;
  Xaa13 is Ala or Gln;
  Xaa14 is Ala, Leu, Ile, pentylglycine, Val, or Met;
  Xaa15 is Ala or Glu;
  Xaa16 is Ala or Glu;
  Xaa17 is Ala or Glu;
  Xaa19 is Ala or Val;
  Xaa20 is Ala or Arg;
  Xaa21 is Ala, Leu, or Lys-NHε-R, wherein R is Lys, Arg, or a C1-C10 straight chain or branched alkanoyl;
  Xaa22 is Ala, Phe, Tyr, or naphthylalanine;
  Xaa23 is Ile, Val, Leu, pentylglycine, tert-butylglycine, or Met;
  Xaa24 is Ala, Glu, or Asp;
  Xaa25 is Ala, Trp, Phe, Tyr, or naphthylalanine;
  Xaa26 is Ala or Leu;
  Xaa27 is Ala or Lys;
  Xaa28 is Ala or Asn;
  Z1 is —OH, —NH2, Gly-Z2, Gly Gly-Z2, Gly Gly Xaa31-Z2, Gly Gly Xaa31 Ser-Z2, Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2, wherein Xaa31, Xaa36, Xaa37, and Xaa38 are independently selected from the group consisting of Pro, homoproline, 3Hyp, 4Hyp, thioproline, N-alkylglycine, N-alkylpentylglycine, or N-alkylalanine, Xaa39 is Ser or Tyr, and Z2 is —OH or —NH$_2$,
  provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala; and when Xaa1 is His, Arg, or Tyr, one or more of Xaa3, Xaa4, and Xaa9 are Ala;

(Chemical Formula II)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

X1-Z1, wherein
  Xaa1 is His, Arg, Tyr, Ala, Norval, Val, Norleu, or 4-imidazopropionyl;
  Xaa2 is Ser, Gly, Ala, or Thr;
  Xaa3 is Ala, Asp, or Glu;
  Xaa4 is Ala, Norval, Val, Norleu, or Gly;
  Xaa5 is Ala or Thr;
  Xaa6 is Ala, Phe, Tyr, or naphthylalanine;
  Xaa7 is Thr or Ser;
  Xaa8 is Ala, Ser, or Thr;
  Xaa9 is Ala, Norval, Val, Norleu, Asp, or Glu;
  Xaa10 is Ala, Leu, Ile, Val, pentylglycine, or Met;
  Xaa11 is Ala or Ser;
  Xaa12 is Ala or Lys;
  Xaa13 is Ala or Gln;
  Xaa14 is Ala, Leu, Ile, pentylglycine, Val, or Met;
  Xaa15 is Ala or Glu;
  Xaa16 is Ala or Glu;
  Xaa17 is Ala or Glu;

Xaa19 is Ala or Val;
Xaa20 is Ala or Arg;
Xaa21 is Ala, Leu, or Lys-NHε-R, wherein R is Lys, Arg, a C1-C10 straight chain or branched alkanoyl, or cycloalleyl-alkanoyl;
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
X1 is Lys Asn, Asn Lys, Lys-NHε-R Asn, Asn Lys-NHε-R, Lys-NHε-R Ala, or Ala Lys-NHε-R, wherein R is Lys, Arg, a C1-C10 straight chain or branched alkanoyl, or cycloalkylalkanoyl;
Z1 is —OH, —NH2, Gly-Z2, Gly Gly-Z2, Gly Gly Xaa31-Z2, Gly Gly Xaa31 Ser-Z2, Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2, wherein Xaa31, Xaa36, Xaa37, and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr, and Z2 is —OH or —NH$_2$,
provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala; and when Xaa1 is His, Arg, Tyr, or 4-imidazopropionyl, at least one of Xaa3, Xaa4, and Xaa9 is Ala.

7. A method of preparing an exendin-containing controlled-release microsphere with a coating layer, the method comprising the steps of:
preparing a core by mixing an exendin and a biodegradable polymer to form an emulsion or a homogeneous mixture;
solidifying the formed emulsion or homogeneous mixture to prepare a primary microsphere; and
suspending the prepared primary microsphere in an aqueous solution comprising 0.02 to 1.0%(w/w) PVA and one or more selected from the group consisting of arginine, lysine, histidine, creatine, creatinine, and urea as a coating material for controlling initial burst of the exendin, to form a coating layer on the microsphere,
wherein:
the solidifying step is performed by a phase-separation method or a spray drying method;
a concentration of the aqueous solution comprising the coating material is from 0.01 M to 1 M;
the biodegradable polymer is a polymer selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate, a copolymer or a simple mixture of two or more selected from the polymer group, a copolymer of the polymer and polyethylenglycol (PEG), or a polymer-sugar complex where a sugar is coupled with the polymer or the copolymer;
the prepared microsphere releases 5% or less than 5% of a total weight of the exendin from the microsphere in the first hour; and wherein the exendin is one or more selected from the group consisting of exendin-3 (SEQ ID NO: 1), exendin-4 (SEQ ID NO: 2), one represented by Chemical Formula I or II, an exendin derivative having a C-terminus substituted or non-substituted with an amide group, and a pharmaceutically acceptable salt thereof:

(Chemical Formula I)
Xaa1 Xaa2 Xaa3 Xaa4 Xaa5 Xaa6 Xaa7 Xaa8 Xaa9 Xaa10
Xaa11 Xaa12 Xaa13 Xaa14 Xaa15 Xaa16 Xaa17 Ala
Xaa19 Xaa20 Xaa21 Xaa22 Xaa23 Xaa24 Xaa25 Xaa26
Xaa27 Xaa28 -Z1, wherein
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHε-R, wherein R is Lys, Arg, a C1-C10 straight chain or branched alkanoyl, or cycloalleyl-alkanoyl;
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
Xaa27 is Ala or Lys;
Xaa28 is Ala or Asn;
Z1 is —OH, —NH2, Gly-Z2, Gly Gly-Z2, Gly Gly Xaa31-Z2, Gly Gly Xaa31 Ser-Z2, Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2, wherein Xaa31, Xaa36, Xaa37, and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr, and Z2 is —OH or —NH$_2$,
provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26, Xaa27, and Xaa28 are Ala; and when Xaa1 is His, Arg, Tyr, one or more of Xaa3, Xaa4, and Xaa9 are Ala;

(Chemical Formula II)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Ala

Xaa19 Xaa20 Xaa21 Xaa22 Xaa23 Xaa24 Xaa25 Xaa26

X1-Z1,

Wherein
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHε-R, wherein R is Lys, Arg, a C1-C10 straight chain or branched alkanoyl, or cycloalleyl-alkanoyl;
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
X1 is Lys Asn, Asn Lys, Lys-NHε-R Asn, Asn Lys-NHε-R, Lys-NHε-R Ala, or Ala Lys-NHε-R, wherein R is Lys, Arg, a C1-C10 straight chain or branched alkanoyl, or cycloalkylalkanoyl;
Z1 is —OH, —NH2, Gly-Z2, Gly Gly-Z2, Gly Gly Xaa31-Z2, Gly Gly Xaa31 Ser-Z2, Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2, wherein Xaa31, Xaa36, Xaa37, and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr, and Z2 is —OH or —NH2,
provided that no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala; and when Xaa1 is His, Arg, Tyr, or 4-imidazopropionyl, at least one of Xaa3, Xaa4, and Xaa9 is Ala.

8. A controlled-release microsphere prepared by the method of claim 6 and comprising:
the core consisting essentially of the exendin as an active ingredient, and the biodegradable polymer; and
the coating layer that coats the core and comprises the coating material,
wherein:
an amount of the exendin is from 0.1 to 10 parts by weight based on 100 parts by weight of the microsphere; and
an amount of the coating layer is from 0.01 to 5 parts by weight based on 100 parts by weight of the microsphere.

9. A controlled-release microsphere prepared by the method of claim 7 and comprising:
the core consisting essentially of the exendin as an active ingredient, and the biodegradable polymer; and
the coating layer that coats the core and comprises the coating material,
wherein:
an amount of the exendin is from 0.1 to 10 parts by weight based on 100 parts by weight of the microsphere; and
an amount of the coating layer is from 0.01 to 5 parts by weight based on 100 parts by weight of the microsphere.

10. A method of preparing the exendin-containing controlled-release microsphere of claim 1, the method comprising the steps of:
preparing the core by mixing the exendin and the biodegradable polymer to prepare a W/O type emulsion or a homogeneous mixture; and
emulsifying by adding the emulsion or the homogeneous mixture to an aqueous solution comprising the coating material to form the coating layer,
wherein a concentration of the aqueous solution comprising the coating material is from 0.01 M to 1 M.

11. A method of preparing the exendin-containing controlled-release microsphere of claim 1, the method comprising the steps of:
preparing the core by mixing the exendin and the biodegradable polymer to form an emulsion or a homogeneous mixture;
solidifying the formed emulsion or homogeneous mixture to prepare a primary microsphere; and
suspending the prepared primary microsphere in an aqueous solution comprising the coating material to form the coating layer on the microsphere,
wherein:
the solidifying step is performed by a phase-separation method or a spray drying method; and
a concentration of the aqueous solution comprising the coating material is from 0.01 M to 1 M.

* * * * *